United States Patent [19]
Bory

[11] Patent Number: 5,822,208
[45] Date of Patent: Oct. 13, 1998

[54] METHOD AND APPARATUS FOR PREDICTING ERRORS IN A MANUFACTURING PROCESS

[75] Inventor: William H. Bory, Baltimore, Md.

[73] Assignee: Bay Instrumentation & Technology Co., Baltimore, Md.

[21] Appl. No.: 767,006

[22] Filed: Dec. 17, 1996

Related U.S. Application Data

[63] Continuation of Ser. No. 229,608, Apr. 12, 1994, abandoned.

[51] Int. Cl.$^6$ .................................................. G06F 19/00
[52] U.S. Cl. ............................... 364/468.15; 364/468.17; 382/141; 382/143
[58] Field of Search ......................... 364/468.01, 468.15, 364/468.16, 468.17, 471.01, 471.02, 469.01, 474.19, 550, 551.01, 552, 554, 556, 561–563; 382/141, 143, 152; 493/6–8, 10–12, 37, 51, 52, 124, 125

[56] References Cited

U.S. PATENT DOCUMENTS

| | | | |
|---|---|---|---|
| 4,893,346 | 1/1990 | Bishop | 382/8 |
| 5,007,096 | 4/1991 | Yoshida | 382/8 |
| 5,046,111 | 9/1991 | Cox et al. | 382/8 |
| 5,146,510 | 9/1992 | Cox et al. | 382/8 |
| 5,189,863 | 3/1993 | Pozzi | 53/411 |
| 5,208,870 | 5/1993 | Ennis | 382/30 |
| 5,212,656 | 5/1993 | Clary et al. | 364/552 |
| 5,365,595 | 11/1994 | Dante et al. | 382/8 |

OTHER PUBLICATIONS

Configurable Vision Input Module manufactured by Allen–Bradley.
Beyond Charts and Graphs by M. Arzoumanian, reprinted from paperboard Packaging, Jan. 1993.
Quality System Solutions by Stochos Inc., 1968.
Comprehensive and EAsy to Use Statistical Process Control Software, Custom/QC Software from Stochos.

*Primary Examiner*—Paul P. Gordon
*Assistant Examiner*—Thomas E. Brown
*Attorney, Agent, or Firm*—Lowe Hauptman Gopstein Gilman & Berner

[57] ABSTRACT

An inspection system for a variety of products, and in particular flat-folded corrugated boxes uses real-time statistical processing control. This control allows graphs to be derived from which to develop trends indicative of future flaws in the products. These flaws are automatically corrected once a trend has been established. Glue marks on flat-folded corrugated boxes are identified and measured by means of pixel count, thereby providing very accurate depiction of the amount of glue on a box so that accurate comparison to a standard configuration can be made.

25 Claims, 6 Drawing Sheets

METHOD AND APPARATUS FOR PREDICTING ERRORS IN A MANUFACTURING PROCESS

This application is a continuation of application Ser. No. 08/229,608 filed Apr. 12, 1994 now abandoned.

TECHNICAL FIELD

The present invention relates generally to error or flaw detection of products on a fast-moving production line. More particularly, this invention relates to the prediction and thus, prevention of flaws or errors in real-time for a manufacturing process for producing corrugated boxes from blanks.

BACKGROUND ART

There are many manufacturing processes from which end products are made by cutting, molding or shaping blanks of the material from which the product is made. Materials from which such products are made include plastic, rubber, paper and sheet metal of various types. Preferably such products are manufactured using a high speed line for carrying out each of the steps of the process necessary to arrive at the final product.

An example of one such manufacturing process is the production of flat-folded corrugated boxes from blanks of corrugated material. The process of cutting and forming of the blanks is well known in this art and need not be further elaborated upon in this application. The final product is a box made of corrugated paper material cut and folded out flat to be later assembled into a box. The boxes are normally shipped in the folded state for later customer use, at which time the boxes are folded into their final three-dimensional shape.

Typically such boxes have characteristics such as size, shape and gap between adjacent cut sections. During the inspection process, these characteristics are measured and compared with an ideal set of measurements to determine if the box is flawed or acceptable. Using photodetection imaging, the size and shape of the box can be checked against predetermined measurements by comparing lines at various parts of an image of the box with predetermined lines programmed into a processor such as the Configurable Vision Input Module (CVIM) manufactured by Allen-Bradley. A copy of a product overview for the CVIM is attached hereto and incorporated by reference into this application along with the instruction manual for using the CVIM. This manual is not attached to this application due to its substantial size and the relatively small advantage the manual gives to the understanding of the present invention.

The CVIM can also be used to check the skew of the various parts of a flat-folded corrugated box with respect to one another. This is done by deriving lines from the box image of adjacent but separate parts and measuring the distance between those parts. This distance is compared to a preprogrammed distance corresponding to the particular box part being inspected to determine if the difference falls within acceptable parameters.

A large variety of different types of measurements are possible using the CVIM unit, including overall shape, overall size, the location of glue marks, the location and density of printing, as well as the direction of all cuts and folds. Thus, the CVIM, as indicated in the attached publication, is capable of producing outputs with respect to thirty-two different measurement comparisons.

However, in a real manufacturing process, an operator is made aware of a flaw in a finished product only after it has gone through the line and is being stacked with other boxes. The CVIM will indicate which of the boxes in the stack of flat-folded boxes are outside of acceptable parameters. These boxes must then be sorted out by hand to remove those indicated as being flawed by the CVIM. To facilitate the removal of flawed boxes, the tail-end of each box is sprayed with a UV dye whenever a problem or flaw in the box is detected by the CVIM. This is discussed in the Paper Board Packaging publication dated January 1993. This publication is hereby incorporated by reference and is attached to the present application.

The information regarding all of the boxes in a product run can be output from the CVIM and stored for later analysis.

This data can also be subjected to statistical process control using a software configuration such as that sold by Stochos Incorporated. A publication describing the Stochos system is attached to this application and incorporated herein by reference. This software permits various statistical analysis techniques to be applied to data from the CVIM. The most prevalent type of analysis results in a graph of difference measurement versus time. This graph can be used for every box in a run or for only those selected on the basis of statistical analysis, for example, one box in five, one box in ten or one box in fifteen. As a result, an operator can view a graph illustrating any of thirty-two measurements for boxes that have been produced in an ongoing production cycle.

As each box is inspected, the selected box measurements will be reflected in the graph. Thus, the graph constantly changes, and is updated in accordance with the most current piece of product being manufactured. The statistical process control programming as disclosed in the attached publication, has the capability of displaying each of the possible thirty-two measurement values at one time for a particular box. The subject software also has the capability of constantly updating average measurements for all of the boxes already manufactured in the production run.

While the operator can be shown everything that has happened on a given production run for any particular aspect of any particular box or all of the boxes, the operator still has no way of absorbing and using this knowledge quickly enough to effect the current production run. The operator is limited to stopping the blanks from being fed into the production line if the operator decides that too many flaws have occurred. For the most part, the data displayed to the operator would be analyzed at a later time for a study of methods to correct conditions in the production process that may lead to flaws.

However, even with the graphs displayed to the operator, there is generally little way of altering the production run to lessen the possibility of flaws or errors. The operator may be selecting the wrong measurements or graphs to observe, and very often the operator is simply not fast enough to make the required adjustments in the machinery to prevent flaws before they occur. The statistical analysis data as it is currently used is limited to analysis after a production run has been made to determine what may be done to eliminate flaws. However, the flaws of the latest production run have already been made, and there is nothing to do but eliminate those boxes which are unacceptable.

DISCLOSURE OF THE INVENTION

One object of the present invention is to apply statistical analysis to product characteristics as they are being inspected during a production run.

Another object of the present invention is to perform flaw prediction on a real-time basis during a production run so the corrections can be made in the processing equipment before product flaws occur.

A further object of the present invention is to provide operator-usable comprehensive data on multiple aspect of product inspection for each of a group of products sampled from the production run and stored in a form readily usable by those controlling the process operation.

An additional object of the present invention allows the data taken during the production run to be accessed by customers for whom the product is intended through a landline network.

Still a further object of the present invention is to use a new and more accurate technique for inspecting glue areas of a corrugated box.

Still a further object of the present invention is the creation of production run histories including critical data indicative of impending errors in a production run.

The aforementioned objects of the present invention are carried out by means of a production inspection and control system which monitors a range of measurements within the parameters indicative of product error or flaw and outside the range of measurements considered indicative of optimum product characteristics. These measurements are subjected to statistical analysis and a trend is predicted regarding the type of flaw that will probably occur if the trend continues. Responsive to the prediction of the flaw, appropriate correction is made in the manufacturing machinery or blanks from which the product is made to reverse the indicated trend and avoid the production error before it occurs.

Another technique for improved inspection performance is the use of an imager to detect the full extent of glued areas by means of a pixel count. This is preferably effected by use of a second camera located well upstream (on the manufacturing line) from the first camera used for providing all the other measurements.

BEST MODE FOR CARRYING OUT THE INVENTION

Figure 1:
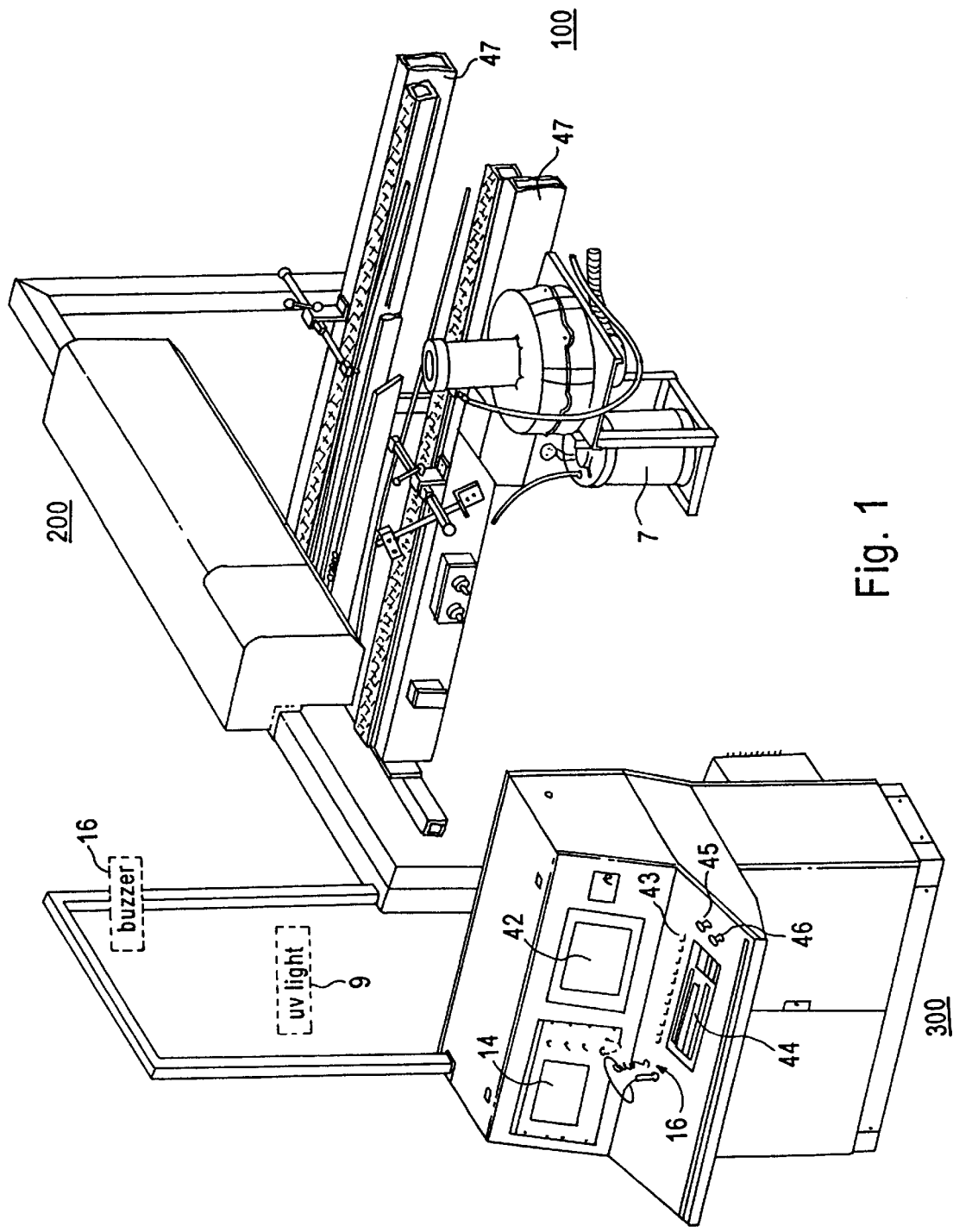
FIG. 1 is a diagram of the processing line, inspection apparatus and control console of the hardware used to carry out the present invention.

FIG. 1 depicts a system used to carry out the operation of the present invention. Three major components are included: production line 100, inspection apparatus 200 and control console 300. The inspection apparatus 200 is suspended above a portion of the production line to facilitate acquisition of a video image of each of the production pieces on the line. The inspection apparatus 200 is connected to console 300 from which the operation of the inspection process, as well as the operation of the processing line 100 is controlled.

Console 300 includes a first cathode ray tube 14 for monitoring the CVIM data including difference measurements between the preprogrammed ideal box measurements and the measurements taken from the images of boxes going through the processing line 100. A light pen 16 and a keyboard 44 are used for programming the console and manipulating certain types of data within the console. Push buttons 43 allow the operator to carry out a number of complex instructions with a single key stroke. Push button 45 is an emergency machine stop for the production line 100 and push button 46 merely stops blanks from being fed onto the production line 100 while still keeping the production machinery of the production line in operation.

The production line as shown includes rails 47 constituting the major support for the other mechanisms on the production line. These are well known in the art and will vary from product to product. Thus, it is not necessary to further distinguish the production line 100 for the case of flat-folded corrugated boxes as opposed to other types of products admitting to inspection and control by the present invention. One common aspect in the production of flat-folded corrugated boxes is the use of ultra-violet liquid applied to those boxes found to be flawed. In FIG. 1, canister 7 is a holding vessel for ultra-violet liquid which is selectively sprayed on those boxes indicated as being flawed by the control system contained within console 300. Every time a flawed box is detected, a buzzer 16 is operated to alert the operator. Ultra-violet light 9 (located further downstream on the production line) is used to point out those boxes which have been sprayed with the ultra-violet liquid. Such boxes are then removed by the operator after stopping either the production line or the input of blanks to the production line.

Figure 2:
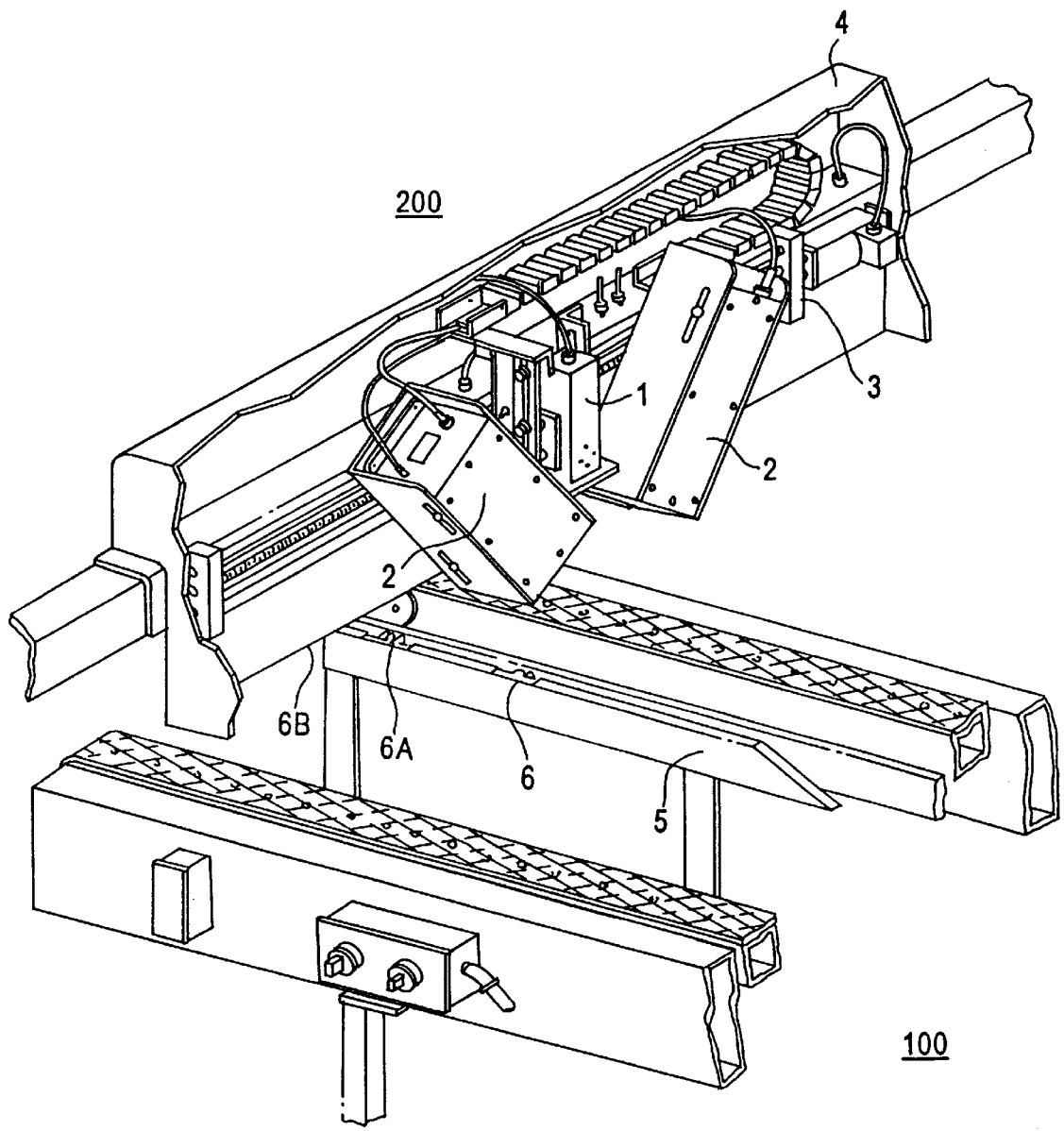
FIG. 2 is a detailed view diagram of the inspection mechanism and a portion of the processing line.

FIG. 2 depicts a more detailed view of inspection apparatus 200 with respect to processing line 100. The key element in the inspection device is camera 1, operating to produce a digitized image of each box passing beneath hood 4 which supports the inspection apparatus. The camera is preferably a CCD device well known in the art of electronic imaging. However, other photosensitive arrangements can be used. High speed imagery of the moving flat-folded boxes is facilitated by the use of dual strobe lights 2. The camera and strobe lights can be moved perpendicular to the axis of processing line 100 by means of a sliding base 3. The sliding base 3 is also arranged to permit the limited movement of the camera and strobe arrangement along the axis of processing line 100 in order to facilitate proper alignment with flat-folded boxes which are skewed on the production line.

As is well known in the art of taking measurements of moving pieces, photo-electric detectors 6, 6a and 6b are mounted along various parts of the production line 100 to facilitate timing of the process of imaging a inspecting each of the boxes. Trigger bar 5 is also used as part of the well known timing scheme.

During the manufacturing process, the boxes move along rails 47. The boxes are printed, scored and slotted. Then the boxes are glued and the folding process has started. As each box moves down the rails 47, the box will pass over top of the trigger bar 5 and will trigger the operation of photo-electric detectors 6, 6a and 6b. The portion of the box to be inspected can be selected by the use of push buttons 43 so that photodetector 6 is used to measure the leading edge of the box, photodetector 6a is used to take a measurement somewhere in the body of the box while photo-electric detector 6b is used to measure from the trailing edge of the box.

The photodetectors send signals to the programmable logic controller (PLC) 28 contained within console 300. The PLC which is responsible for all the logic control of the system, sends a signal to the Vision I/O board 18 (shown in FIG. 4).

As previously indicated, CRT 14 is used to display the data handled by the CVIM, as well as data sent to the Vision I/O board 18. Once an image of the box is displayed on CRT 14, the image will be referenced to a reference line gauge, having all of the line gauges and windows inspect the box. Temperature protection is provided by means of temperature switch 33. A second alarm buzzer 40 is also provided for the convenience of the operator.

Figure 3:
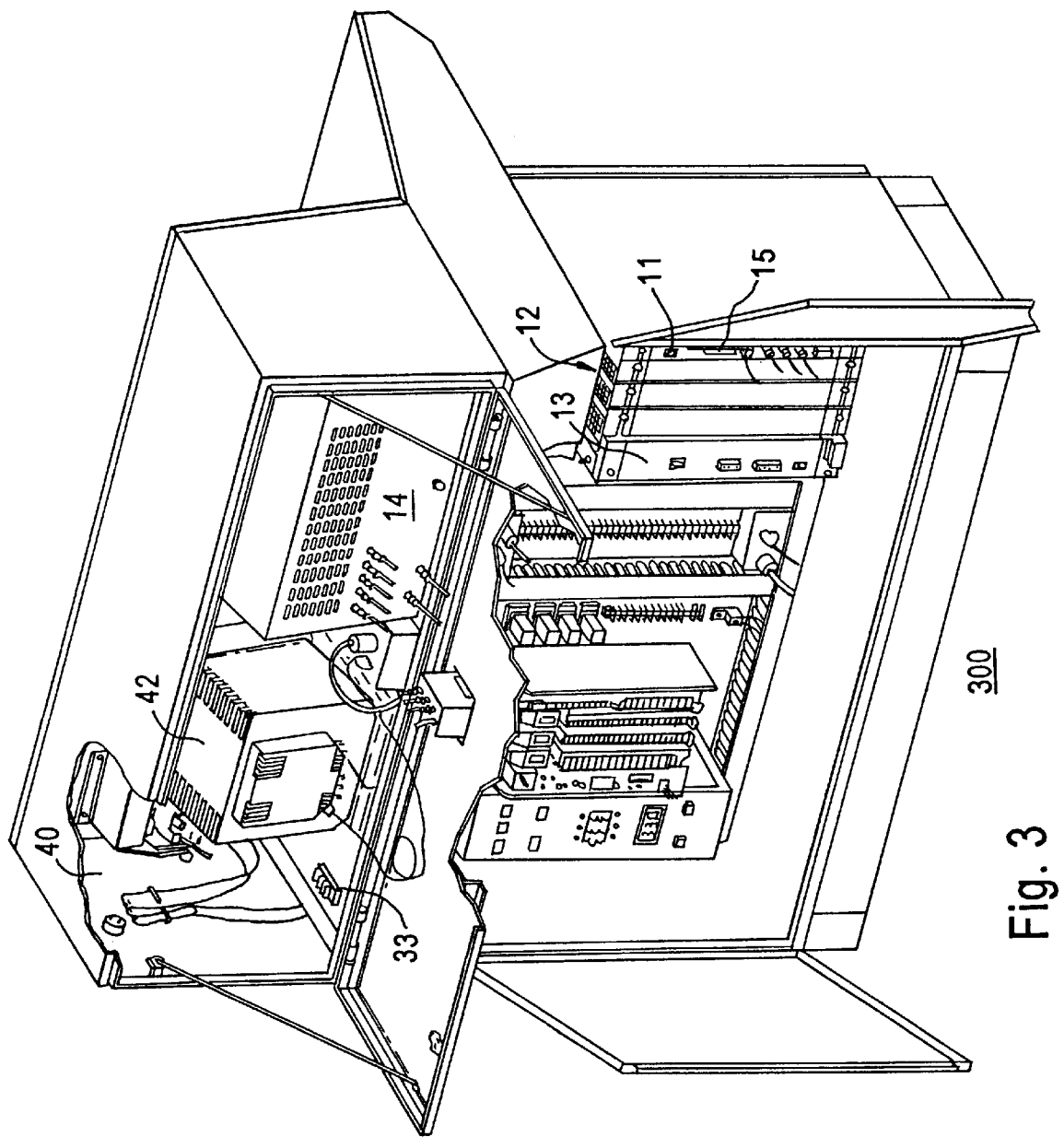
FIG. 3 is a rear interior view diagram of the control console.
Figure 4:
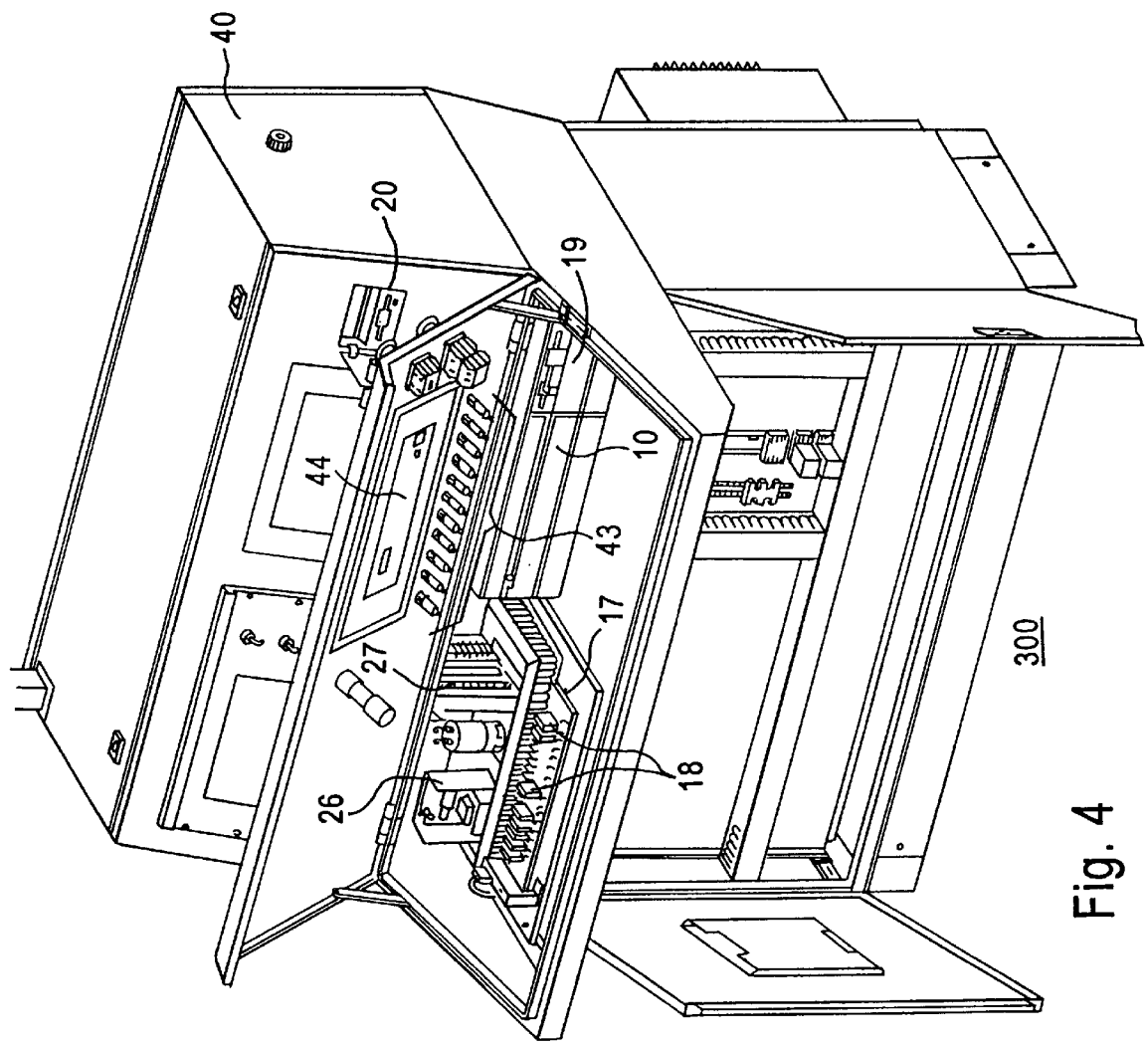
FIG. 4 is a front interior view of the control console.

FIG. 3 further depicts CRT 42 used with a personal computer (PC) 10 as depicted in FIG. 4 for operating the statistical process control software. The PC 10 also includes floppy drive 20, as well as SI card 19. The PC 10 is preferably a model 386. However, more powerful models can be used. Also contained with the personal computer are Vision I/O board 17 and Vision I/O modules 18, as well as power supplies 26 and 27 necessary for the operation of certain system components. The PLC as used with the present invention is capable of keeping track of ten boxes at a time.

The personal computer 10 uses the Stochos statistical processing control software to keep track and manipulate the data measured using the CVIM. Personal computer 10 can also be used to program measurement parameters for ideal models of products to be manufactured into the CVIM by means of the SI software contained in the PC. Once such parameters are established, they can be entered automatically so that the operator does not have to reprogram the CVIM.

FIG. 3 depicts a rear view of the interior of control console 300. The CVIM module 11 controls the comparison of predetermined standards to the images of boxes passing beneath the inspection apparatus 200. The CVIM module includes component racks 12, power supply 13 and a RAM card 15 is used for adding additional programming to the CVIM. However, the CVIM can also be programmed by downloading predetermined standards for each type of product to be manufactured from another computer. Such a computer can be part of the control console or hard wired to the control console from a remote location. Data can also be entered into the CVIM from a remote location by means of a communication network such as a standard telephone landline system.

An additional camera configuration such as that shown in FIG. 2 can be added at a point substantially upstream on the production line 100 from the first camera originally described, supra. This second camera is dedicated to determining the extent of those areas containing glue on each box. Consequently, such detection must take place at a point in the manufacturing process before the glued areas are covered up by other portions of the box. In prior art arrangements, the area covered with glue is determined using moisture detectors. In contrast, the present invention requires that a video image of the area containing glue be taken. Pixels corresponding to the areas covered with glue are then counted, and a comparison made with a predetermined standard or ideal against which the measured values are compared. Such a technique can be used by itself, or can be used in conjunction with the first video imager described, supra. Unlike the remainder of the present invention, this technique is dedicated to products requiring glue.

Figure 5:
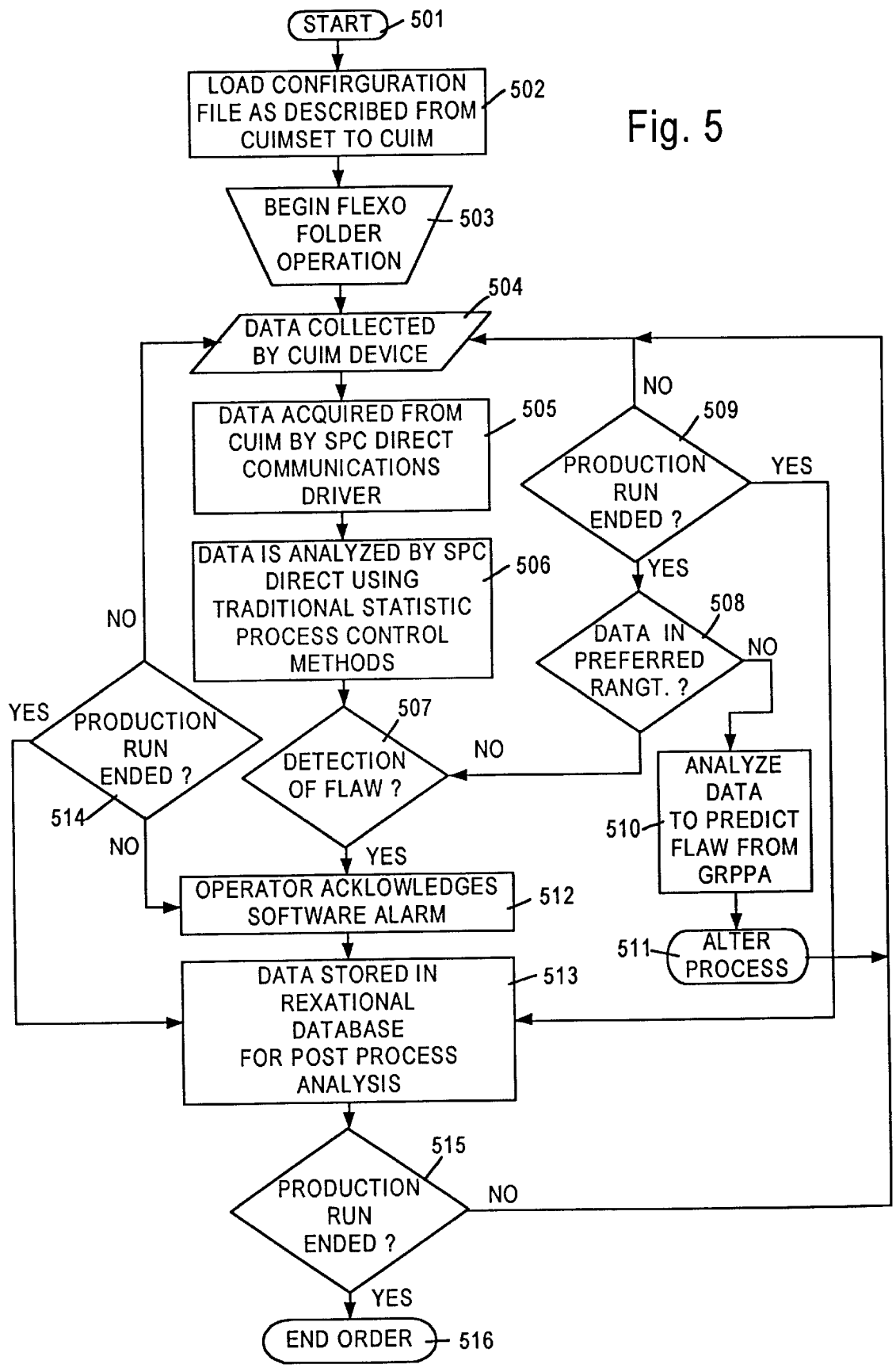
FIG. 5 is a flow diagram depicting the operation of the present invention.

FIG. 5 is a flow diagram depicting the operation of the present invention. At step 501, the operator starts both the control panel and the processing line to begin manufacture of the subject product, such as flat-folded corrugated boxes. During this step, the blanks are positioned to be sent down the manufacturing line and the various sensors needed to track the positions of the blanks as they are manufactured into boxes are also activated.

At step 502, the parameters defining the configuration of the type of box to be manufactured is loaded from the PC or other storage device into the CVIM. These parameters will serve as the standard against which the images of each box are measured to determine flaws, and to develop the characteristic graphs indicative of future flaws. Once the relevant data has been placed into the CVIM, the manufacturing process begins at 503. The blanks are folded, slotted and glued in a manner well known in this technology to transform the blanks into flat-folded corrugated boxes.

As each box passes the inspection device 200, data is collected by the CVIM device, as indicated at step 504. As previously stated, the data collected can be of thirty-two different measurements of the box and its characteristics as reflected by a digital image formed of each box by camera 1. The CVIM carries out the comparison between the ideal parameters fed into the CVIM at step 502 and the measurements derived from the image of each of the flat-folded boxes.

At step 505, the comparison data is acquired from the CVIM by statistical processing control software (SPC) in the personal computer 10. This software analyzes all measurements to determine the presence of a flaw or error for each of the boxes. The software also samples a predetermined number of difference measurement for a predetermined fraction of all the boxes in a manufacturing run. For example, the SPC software can sample one in five boxes, one in ten boxes or one in fifteen boxes. Preferably, the SPC samples those measurements most crucial to the type of box or other product being produced.

Figure 6:
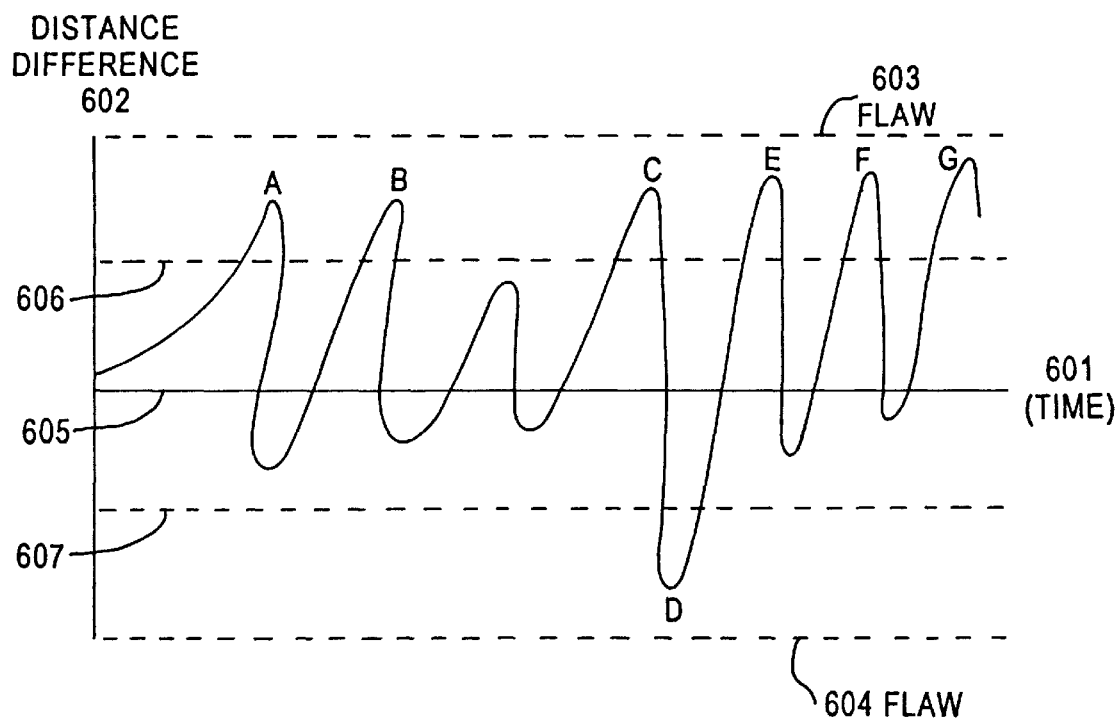
FIG. 6 is a graph depicting representative readings used for statistical analysis.

The measurements from the sample boxes are then analyzed at step 506 and a graph similar to that found in FIG. 6 is derived. The graph of FIG. 6 is a plot of distance difference measurements (along axis 602) versus time (along axis 601). Axis 605 represents the ideal measurement, i.e., no distance between the ideal parameter and the measurements taken from the image of a box under analysis. The distance difference range as marked by 603 and 604 indicate distance measurements at (and beyond) which a flaw in the subject box is deemed to exist. The ranges marked from 606 to 603, and from 607 to 604, respectively, are considered ranges of questionable values. While this range is considered acceptable, it is not highly desirable.

At step 507, a determination of a flaw is made if any of the measurements go beyond the range marked by lines 603 or 604. It is noted that these ranges can change for different measurements (at different portions of the box) and for different types of boxes. Assuming that a flaw is not detected, the process proceeds to step 508. At this step, a determination is made if the measurements are within the preferred range (from 605 to 606, and from 605 to 607, respectively). If this is the case, the process proceeds to step 509 where determination is made if the production run is ended. If the production run has ended, the process moves to step 514 and the data gathered by the CVIM throughout the production run is stored for future use. This is done by the PC which stores the data in its core memory or can place the subject data in removable memory devices such as a RAM card. The stored information can also be downloaded via a network to other storage devices. If the production run at step 509 has not ended, the process moves to step 504 where additional data is collected for each of the additional flat-folded boxes to be inspected.

If the measurements checked at step 508 are not within the preferred range but are in the ranges marked by 606 to 603 and 607 to 604, respectively, these measurements are then further analyzed. Using well known statistical processes, a trend is derived from the measurements indicated as A–G in FIG. 6. This trend is analyzed to determine where a flaw is likely to occur next. The type of flaw is analyzed at step 510 using standard statistical methods as well as well known knowledge of what normally causes such tendencies as those predicted by the graph.

With the cause of the problem derived using the trend from the graph, appropriate preprogrammed responses can be activated so that a correction is made in the manufacturing process at step 511. Such corrections normally take the form of adjusting the blanks from which the flat-folded boxes are made. Such adjustments may also take the form of changing machine parameters for cutting, gluing and folding. The response that is made depends upon the trend in each of the sampled graphs, and the type of measurement from which the graph is derived.

The data regarding the meaning of trends for certain types of measurements and the appropriate responses to such trends can be preprogrammed along with the configuration and parameter data fed into the CVIM at step 502. The subject statistical analysis data would then be fed through the personal computer at step 505. However, such data could remain with the personal computer which normally downloads configuration data to the CVIM. Once the manufacturing process has been altered, data is once again collected at step 504 and the detection process of FIG. 5 continues.

If a flaw is detected at step 507, an alarm is sounded and operator is required to acknowledge the alarm at step 512. If the operator has not acknowledged the alarm, an additional check is made to see if the production run has ended at step 514. If so, the process moves to step 513 where the entire data of the production run is stored. If on the other hand, the production run has not ended, the process returns to step 504 for the collection of additional data by the CVIM. If the operator acknowledges software alarm at 512, the data regarding the flaw is stored for future use at step 513. A check is made at step 515 to determine if the production run has ended. If not, the process returns to step 504 to gather additional data on the remaining boxes to be inspected. If on the other hand, the production run has ended, the process proceeds to step 506. At which time, blanks are no longer being fed into the production line, and the operator receives additional instructions regarding the next production run.

While there have been described and illustrated several specific embodiment of the present invention, it will be clear that variations and the details of the embodiments specifically illustrated and described may be made without departing from the true spirit and scope of the invention as defined in the appended claims. In particular, products other than flat-folded corrugated boxes can be manufactured using the inspection and control of the present invention.

Further, different control systems can be used for carrying out the present invention. For example, it is possible to allow a customer to view the inspection data from the CVIM via a communications network. It is also possible to substitute a mainframe computer for the PC in each of a plurality of inspection systems. Data storage can be handled in a number of different ways, including RAM card, floppy disk, laser disk or removable magnetic disk drives. Further, set-up parameters can be fed to the CVIM from a variety of different sources and in a variety of different manners.

Although the present invention has been described and illustrated in detailed, it is clearly understood that the same is by way of illustration and example only, and is not to be taken by way of illustration and example only, and is not to be taken by way of limitation. The spirit and scope of the present invention is limited only by the terms of the appended claims.

I claim:

1. A method for adjusting a process for manufacturing products from blanks, said method operating in real-time to avoid defects in said products during said manufacturing process, said method comprising the steps of:
   (a) forming a digital image of each of said products;
   (b) comparing each said image to an ideal predetermined image to derive difference measurements between said ideal predetermined image and each formed image, said comparison taking place at a plurality of selected locations on each of said formed images;
   (c) determining if said difference measurements exceed predetermined parameters indicative of a flawed product;
   (d) sampling difference measurements from a predetermined number of products to form a graph with respect to time versus said difference measurements, said sampled difference measurements falling within a predetermined range indicative of questionable difference measurements;
   (e) applying statistical analysis to said graph to develop a trend indicative of future flaws in future products; and
   (f) adjusting said process responsive to said trend to avoid said predicted future flaws in said future products.

2. The method of claim 1, further comprising the step of:
   (g) storing said difference measurements for a plurality of locations on each said product.

3. The method of claim 2, further comprising the step of:
   (h) storing a graph of selected difference measurements for selected products.

4. The method of claim 3, wherein said plurality of difference measurements takes place at thirty-two locations on each said product.

5. The method of claim 3, further comprising the step of:
   (i) displaying said difference measurements for each of said locations on each of said products.

6. The method of claim 5, further comprising the step of:
   (j) displaying said graph for each of said sampled measurements.

7. The method of claim 1, wherein at least one of said difference measurements is constituted by a comparison of ink density on a sampled product.

8. The method of claim 1, wherein step (c) comprises the sub-step of marking each flawed product with ultra-violet ink.

9. The method of claim 1, wherein step (a) further comprises a preliminary step of inputting data indicative of an ideal image of a product to be manufactured, a range indicative of a flawed product and a range indicative of a questionable product.

10. The method of claim 9, wherein step (a) further comprises the sub-step of determining a position of each blank and adjusting an imager to compensate for variations in blank position.

11. The method of claim 8, wherein step (c) further comprises the sub-step of displaying an indication to an operator each time a flawed product is detected.

12. The method of claim 11, wherein step (c) further comprises the sub-step of stopping blanks from being processed upon detection of a predetermined number of flawed products.

13. An apparatus for controlling a process for manufacturing products from blanks, said apparatus operating in real-time to avoid defects in said products during said manufacturing process, said apparatus comprising:

(a) a digital imager;

(b) means comparing each said image to an ideal predetermined image to derive difference measurements between said ideal predetermined image and each formed image, said means for comparing operating at derived difference measurements at a plurality of selected locations on each of said formed images;

(c) means for determining if said difference measurements exceed predetermined parameters indicative of a flawed product;

(d) means for sampling difference measurements from a predetermined number of products to form a graph with respect to time versus said differences measurements, said means for sampling difference measurements operating to select difference measurements within a predetermined range indicative of questionable difference measurements;

(e) means for applying statistical analysis to said graph to develop a trend indicative of future flaws in future products; and (f) means for adjusting said blanks responsive to said trend to avoid said predicted future flaws in said future products.

14. The apparatus of claim 13, further comprising:

(g) means for storing said difference measurements for a plurality of locations on each said product.

15. The apparatus of claim 14, further comprising:

(h) means for storing a graph of difference measurements for each said location.

16. The apparatus of claim 15, wherein said means for comparing derived difference measurements for thirty-two locations on each said product.

17. The apparatus of claim 15, further comprising:

(i) means for displaying said difference measurements for each of said locations on each of said products.

18. The apparatus of claim 17 further comprising:

(j) means for displaying said graph for each of said sampled measurements.

19. The apparatus of claim 13, wherein at least one of said difference measurements is constituted by a comparison of ink density on a sampled product.

20. The apparatus of claim 13, further comprising:

means for marking each flawed product with ultraviolet ink.

21. The apparatus of claim 13, further comprising means for inputting data indicative of an ideal image of a product to be manufactured, a range indicative of a flawed product and a range indicative of a questionable product.

22. The apparatus of claim 21, further comprising means for determining a position of each blank and adjusting an imager to compensate for variations in blank position.

23. The apparatus of claim 22, further comprising means for displaying an indication to an operator each time a flawed product is detected.

24. The apparatus of claim 23, further comprising means for stopping blanks from being processed upon detection of a predetermined number of flawed products.

25. The apparatus of claim 13, further comprising a second digital imager arranged to form a digital image of areas of each said box containing glue;

means for counting pixels corresponding to said areas containing glue on each said box; and means for comparing said pixel count corresponding to said areas containing glue to a predetermined ideal pixel count.

* * * * *